United States Patent [19]

Jorde

[11] Patent Number: 5,102,387
[45] Date of Patent: Apr. 7, 1992

[54] TRANSPORTABLE DOUCHE ATTACHMENT

[76] Inventor: Edward P. Jorde, Cottage Pl., Box 103, Granite Springs, N.Y. 10527

[21] Appl. No.: 697,676

[22] Filed: May 9, 1991

[51] Int. Cl.$^5$ ............................................. A61M 3/04
[52] U.S. Cl. ................................... 604/39; 604/150; 604/262
[58] Field of Search ..................... 604/39, 150, 262

[56] References Cited

U.S. PATENT DOCUMENTS

| | | | |
|---|---|---|---|
| 1,779,268 | 10/1930 | Belfrage et al. | 604/39 |
| 1,940,210 | 12/1933 | Frederick | 604/150 X |
| 3,162,193 | 12/1964 | Zacks | 604/262 |
| 3,162,197 | 12/1964 | Erteszek | 2/73 X |
| 3,461,870 | 8/1969 | Van Linge | 604/150 X |
| 3,769,977 | 11/1973 | Victory | 604/150 |
| 3,817,247 | 6/1974 | Mills | 604/150 |
| 3,847,150 | 11/1974 | Scheuermann | 604/150 X |
| 3,921,635 | 11/1975 | Gauthier | 604/150 X |
| 4,000,742 | 1/1977 | Diglacomo | 604/150 X |
| 4,642,100 | 2/1987 | Kabbaby | 604/150 |

FOREIGN PATENT DOCUMENTS 2104801  3/1983  United Kingdom ............... 604/150

*Primary Examiner*—William H. Grieb
*Attorney, Agent, or Firm*—Joseph B. Taphorn

[57] ABSTRACT

A douche attachment for easy attachment to a hand held shower heat comprises a nozzle, a cone having its reduced end attached to the nozzle and its enlarged end to engage the outer perimeter of the face of a shower head, and a elongated ring of thin flexible material attached at one end of the enlarged end of the shower head and adapted to be gathered behind the shower head and held in place by a velcro strap. The nozzle is formed of a tubular material having ridges and apertures in the valleys between the ridges. The small end of the cone may be attached to the nozzle by any suitable means and may be further formed to hold a screen in place at the entrance to the nozzle. The cone may be formed of soft vinyl which generally holds its shape but can be yieldably deformed. The thin flexible material may be secured to the enlarged end of the cone by any suitable means. The velcro strap is tightened after the enlarged end of the cone has been placed against the face of the shower head and the thin flexible material arranged over the shower head and its free ends gathered by the velcro strap. After douching, the velcro strap may be loosened and the douche attachment removed and cleaned and compacted and transported for use in another location or storage.

13 Claims, 1 Drawing Sheet

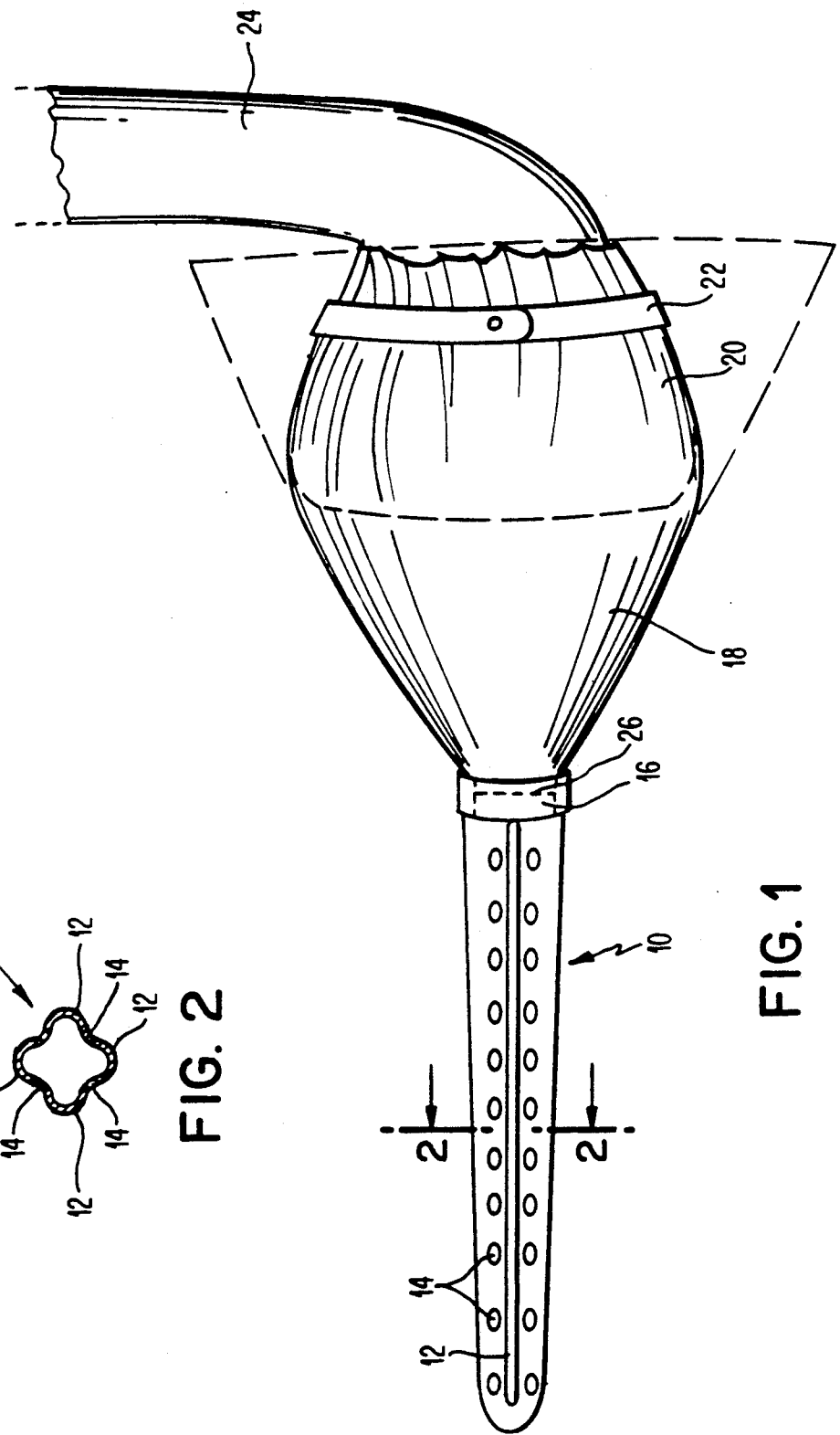

TRANSPORTABLE DOUCHE ATTACHMENT

INTRODUCTION

1. Field of the Invention

This invention relates to douche attachments for shower heads, and more particularly to a douche attachment which will fit any shower head.

2. Prior Art

The prior art includes U.S. Pat. No. 3,162,193; Van Linge U.S. Pat. No. 3,461,870; Mills U.S. Pat. No. 3,817,247; Scheuermann U.S. Pat. No. 3,847,150; Gauthier U.S. Pat. No. 3,921,635; and Kabbaby U.S. Pat. No. 4,642,100.

Zacks shows a douche attachable to a shower head by tying and that includes a bag 16 a portion of which is disposed so as to catch water from the shower head which is then delivered by tubing 20 to a nozzle 21. Van Linge would insert an intermediate pipe 12 between the plumbing of the household and the shower head 13, the intermediate pipe 12 including a valve to divert water to a nozzle 18 via tubing 15. Mills and Scheuermann also include plumbing inserts between the shower head and the plumbing of the house.

Gauthier shows a portable shower head. The free end of the shower head 10 is formed with an annular, radially outwardly extending flange 20 which is adapted to receive a diametrically enlarged, generally cupped-shaped, relatively flexible coupling or attaching skirt 24 integral with a douche tube 22 and having a flexible, angular, radially inwardly turned lip 25 on the marginal edge thereof for engagement behind the flange 20 on the shower head 10 to retain the douche to the shower head. He also shows a fixed shower head having an axially downwardly projecting douche attaching fitting 63 and to which an enlarged, quick-connect coupling 101 on a douche is fitted.

Kabbaby is another one introducing plumbing between the household plumbing and the showerhead to accommodate douche apparatus.

SUMMARY OF THE INVENTION

Accordingly it is an object of the invention to provide a douche attachment for shower heads which does not require any special plumbing.

Another object of the invention is to provide a douche attachment which is usable with any portable shower head.

Still another object of the invention is to provide a douche attachment which is easily attached to any portable shower head.

Still another object of the invention is to provide a douche attachment which is inexpensive of construction.

A still further object of the invention is to provide a douche attachment which is compact and easily transported.

Yet another object of the invention is to provide a simple douche attachment which can also hold a medical pill.

Yet another object of the invention is to provide a douche attachment which is readily reusable.

Another object of the invention is to provide a douche attachment which is easily manufactured.

The objects of the invention are in part achieved through the extensive use of plastics. A plastic nozzle that is centrally apertured has its central aperture communicating through radially extending apertures formed along the length of the nozzle, with areas to be bathed. The supply end of the nozzle is connected to the reduced end of a cone of soft vinyl. The enlarged end of the soft vinyl cone is connected to a light and flexible plastic generally of a cylindrical shape and having at its other or free end an attachment mechanism such as a velcro locking strap. The free end of the cylinder of light plastic would be drawn over a shower head and the velcro locking strap adjusted to where the douche attachment would be secured upon the shower head.

A screen may be placed inside the douche attachment where the nozzle joins the soft vinyl cone to restrain the outward movement of any medicinal tablet which may be placed within the cone to be dissolved during the douching operation.

BRIEF DESCRIPTION OF THE SEVERAL VIEWS OF THE DRAWING

These and other objects, features, and advantages of the invention will become apparent from a reading of the following description, when considered with the appended drawing wherein:

FIG. 1 is a side elevational view of the disposable douche attachment; and

FIG. 2 is a cross-sectional view of the nozzle taken along the line 2—2 of FIG. 1.

DETAILED DESCRIPTION OF THE PREFERRED EMBODIMENT

Referring now to the drawings a nozzle is generally indicated by the number 10. It is a longitudinally extending piece about four inches in length and tapers toward the free end. The nozzle 10 is provided with four ribs or ridges 12 which as best seen in FIG. 2 defines a somewhat rectangularly shaped nozzle in cross-section. The nozzle is formed from tubular material to define a central conduit so that fluids may flow down the inside of it. Apertures 14 are formed in the valleys between the ridges 12 and allow the outflow of water passing down the conduit inside of the nozzle 10.

The other or non-free end of the nozzle terminates in a annular ring 16 which is circular.

Attached to the non-free end of the nozzle is a cone 18 formed of soft vinyl or other yieldable but form holding material, the cone walls being sufficiently thick to generally retain the shape of the cone. The reduced end of the cone engages the annular ring 16 on the non-free end of the nozzle so as to securely hold the two together. The securing may be by various methods such as friction fit, cement, or a lip formed on the reduced end of the cone so as to rest behind the annular ring on the nozzle.

The enlarged end of the cone 18 is secured in any well known manner to the one end of a cylinder of soft flexible material 20. The other or free end of the cylinder of soft flexible material 20 carries on its exterior in any suitable manner a locking strap 22 of velcro or the like. The cylinder of material 22 is intended to fit over the head of a hand held showering device 24.

To accommodate the use of medicinal tablets in showering operations, a screen 26 may be secured in any suitable manner across the end face of the non-free end of the nozzle 10 inside the cone 18.

In installation, the attachment would be placed such that the enlarged end of the soft vinyl cone engages face of the head of the shower device 24. The soft flexible material cylinder 20 would then be arranged behind the head and velcro strap 22 on the free end thereof adjusted so as to tightly embrace the back of the head thereby precluding the douche attachment from leaving the head when water under pressure was admitted to the showering device 24.

In use, after being installed on the head of the portable showering device 24, the douche attachment would be used in normal fashion. Admission of water to the shower head would result in the flow of water from the apertures 14 in the nozzle 10. Any medicinal tablet placed in the cone 18 prior to installation of the douche attachment on the shower head would result in its treatment of the water entering the nozzles 10. It would of course be kept in place and from clogging the nozzle conduit by the screen 26.

Waterproof attachment of the douche attachment to the shower head is not necessary as the device is being used in a place adapted to accommodate water in and around the place, to wit in a shower.

It will be appreciated that the applicant that applicant has invented a device which is compact, portable and easily installed. It can be reused. Parts are inexpensive since they are all made of plastic which can be fabricated in mass quantities from inexpensive materials.

While applicant has shown a preferred embodiment of the invention, it will be understood that other and different embodiments utilizing principles of the invention will be apparent to those skilled in the art. Accordingly it is intended that the invention be defined only by the spirit or scope of the appended claims.

What is claimed is:

1. In a douche attachment, a nozzle, a cone whose reduced end is attached to the non-free end of the nozzle, and a ring of thin flexible material attached at one end to the enlarged end of the cone and adapted at its other end to be gathered behind a shower head.

2. A douche attachment according to claim 1, and means for gathering the free end of the thin flexible material.

3. A douche attachment according to claim 2, wherein the gathering means is a velcro strap.

4. A douche attachment according to claim 1, wherein the cone is formed of a yieldable material.

5. A douche attachment according to claim 4, wherein the yieldable material is soft vinyl.

6. A douche attachment according to claim 1, wherein the nozzle is formed of a tubular material.

7. A douche attachment according to claim 6, wherein the nozzle is constructed with ridges.

8. A douche attachment according to claim 7, wherein apertures are formed in the nozzle in the valleys between the ridges.

9. A douche attachment according to claim 6, wherein the nozzle is tapered towards its free end.

10. A douche attachment according to claim 1 wherein a screen is placed at the entrance to the nozzle from the cone.

11. A structure for attaching a douche nozzle to a shower head comprising a cone having a reduced end for attachment to the nozzle and an enlarged end for attachment to a shower head, and an elongated ring of thin flexible material attached to the enlarged end of the cone for gathering behind a shower head.

12. A structure according to claim 11, and means on the free end of the ring of thin flexible material for gathering the material behind the shower head to hold it in place.

13. A structure according to claim 12, wherein the gathering means is a velcro strap.

* * * * *